United States Patent [19]
Grandin et al.

[11] Patent Number: 4,501,922
[45] Date of Patent: Feb. 26, 1985

[54] AROMATIC AMINES FROM ALKALI METAL AMIDE AMINATING AGENT AND AROMATIC

[75] Inventors: Roland E. Grandin, Alburtis; Barton Milligan, Coplay, both of Pa.

[73] Assignee: Air Products and Chemicals, Inc., Allentown, Pa.

[21] Appl. No.: 509,259

[22] Filed: Jun. 29, 1983

[51] Int. Cl.³ .............................................. C07C 85/00
[52] U.S. Cl. ..................................................... 564/408
[58] Field of Search ........................................ 564/408

[56] References Cited

U.S. PATENT DOCUMENTS

| | | | |
|---|---|---|---|
| 2,000,411 | 5/1935 | Morrell et al. | 44/9 |
| 2,104,407 | 1/1938 | Thomas | 260/130.5 |
| 2,750,417 | 6/1956 | Closson et al. | 564/408 X |
| 2,948,755 | 8/1960 | Schmerling | 564/408 |
| 3,832,364 | 8/1974 | Coulson | 564/408 X |
| 3,919,155 | 11/1975 | Squire | 564/408 X |
| 3,929,889 | 12/1975 | Squire | 564/408 X |
| 4,031,106 | 6/1977 | Del Pesco | 260/296 |

*Primary Examiner*—Paul F. Shaver
*Attorney, Agent, or Firm*—Russell L. Brewer; E. Eugene Innis; James C. Simmons

[57] ABSTRACT

This invention pertains to a process for preparing mononuclear aromatic amines by reacting an alkali metal amide with a mononuclear aromatic compound, e.g., benzene and toluene. The reaction is carried out in the presence of a metallic hydrogenation catalyst, suitably copper, nickel, rhodium or cobalt, the metal being present in an amount sufficient for catalyzing the reaction. The amine then is formed by adding a protonating agent to the resulting reaction product formed by the reaction of the alkali metal amide with the aromatic compound. The addition of the protonating agent liberates the amine.

2 Claims, No Drawings

AROMATIC AMINES FROM ALKALI METAL AMIDE AMINATING AGENT AND AROMATIC

DESCRIPTION OF THE PRIOR ART

Commercially, aromatic amines are generally produced by the mixed phase nitration of the aromatic compound to form the intermediate nitroaromatic followed by the reduction of the nitro group to the amine. Nitration is usually effected by the mixed acid technique which comprises using nitric acid and sulfuric acid as the nitrating agent. The nitro group is then hydrogenated in the presence of a catalyst, e.g. nickel catalyst.

Another technique for producing aromatic amines has been the ammonolysis of halides. In this procedure, an aromatic compound is halogenated using chlorine or bromine as the halogenating agent and then the resultant aromatic halide is reacted with aqueous or alcoholic solutions of ammonia.

U.S. Pat. No. 2,000,411 discloses a procedure for the manufacture of amines using an alkali metal amide. In the process, a halogenated derivative, a sulfonic or a sulfinic derivative of an aromatic compound is reacted with sodium amide. Examples of aromatic reactants include benzyl chloride or benzyl sulfonate or sulfonite.

U.S. Pat. No. 2,104,407 expands upon the disclosure recited in the U.S. Pat. No. 2,000,411 and suggests three techniques for forming aromatic amines described heretofore, i.e., the nitration technique, the ammonolysis of halides, and the use of the alkali metal amide.

U.S. Pat. No. 4,031,106 discloses a direct process for producing an aromatic amine by the reaction of an aromatic compound and ammonia. The reaction is catalyzed by a conditioned nickel/nickel oxide/zirconium oxide catoloreactant containing an oxide of a rare earth metal.

Even through all of the processes recited above are widely used, it is recognized that each process is not chemically or energy efficient. For example, substantial amounts of energy are required in the manufacture of amines via the mixed phase nitration since substantial amounts of water are formed by reduction of the nitro group. The water by-product must be removed from the spent acid as a means for recovering the acid product. The other processes often result in the manufacture of by-products other than the water which are difficult to remove from the product or are difficult to dispose of properly to meet environmental regulations.

SUMMARY OF THE INVENTION

This invention relates to a process for forming a mononuclear aromatic amine by directly aminating the mononuclear aromatic compound via nucleophilic substitution of the hydrogen atom on the aromatic ring. In this reaction, an intermediate reaction product is formed which can then easily be protonated to form the amine. The direct amination is carried out by reacting a mononuclear aromatic compound with an alkali metal amide in the presence of a metallic hydrogenation catalyst, the catalyst being present in an amount sufficient effective for catalyzing the reaction under the conditions utilized. The amine is liberated by adding a protonating agent.

Some of the advantages of the process are:
it provides a direct method for amination since it involves direct nucleophilic displacement of a hydrogen atom as opposed to the nucleophilic displacement of intermediate atoms such as a halogen, nitro and other groups commonly used in the art;
it offers efficiency in terms of raw materials, and it is energy efficient since no water is formed which must be distilled from the system.

DETAILED DESCRIPTION OF THE INVENTION

In accordance with this invention, mononuclear aromatic amines are produced by effecting reaction of a mononuclear aromatic composition with an alkali metal amide. In one sense, the reaction is similar to the Chichibabin reaction involving the amination of pyridine with sodium amide except that pyridine will readily undergo direct nucleophilic substitution of the hydrogen atom with sodium amide. However, sodium amide alone is ineffective for aminating mononuclear aromatic hydrocarbons via nucleophilic substitution of the hydrogen atom.

A procedure has been developed which permits the direct substitution on an aromatic compound as compared to the usual nucleophilic substitution of an amine group for a halogen atom, a sulfonate or sulfinic group pendant from the aromatic ring as performed by the prior art. The mononuclear aromatic compounds which are directly reactable with alkali metal amide in the presence of a catalyst, are those which contain a single benzene ring or those substituted with a lower alkyl group, e.g. from 1 to 3 carbon atoms. Examples of mononuclear aromatic compounds suited for practicing the invention include benzene, toluene, xylene and cumene.

The aminating agent used in the reaction is an alkali metal amide of the formula: MNHR, where R is hydrogen, $C_{1-4}$ alkyl group or aromatic group. Representative examples of an R group include: phenyl, tolyl, methyl, ethyl, propyl and butyl.

Metals (M) in the formula suited for use in the amination reaction are conventional alkali metals such as lithium, sodium, potassium and cesium. Sodium and potassium amides are the two that are usually used in this type of amide for reaction.

As stated previously, in order to effect reaction between the alkali metal amide and mononuclear aromatic compound, a catalytic material must be present in the reaction system an amount sufficient to catalyze the formation of the intermediate reaction product. Although specific analysis have not been made of the intermediate, it is believed the reaction product is an alkali metal salt of the aromatic amine. Hydrogenation catalysts, suitably cobalt, copper and rhodium are sufficiently catalytic to effect the reaction between the alkali metal amide anonuclear aromatic compound. As with conventional hydrogenation catalysts, these hydrogenation catalysts may be carried upon a support. However, most supports are not stable under the reaction conditions and, therefore, support materials are quite limited. One support having stability under the reaction conditions is carbon.

The alkali metal amide is incorporated into the reaction system in at least a stoichiometric quantity for effecting nucleophilic displacement of the hydrogen ion with the amine group. Generally, quantities from one to five moles excess alkali metal amide based upon the mononuclear aromatic compound are utilized.

The temperature which is used in carrying out the reaction is that temperature necessary to effect the formation of the intermediate reaction product, generally from about 200° to 300° C.

After reaction, the intermediate reaction product is contacted with a protonating agent. Its addition to the reaction product results in the formation of an aromatic amine. Typical protonating agents well suited for this reaction are water or aqueous mineral acids. The protonatient is added in amount sufficient to convert the intermediate to the amine. Typically, from 0.01–1, usually 0.1–0.5 moles protonating agent per mole of aromatic compound are added. The protonation is readily effected at temperatures from 10°–50° C.

The catalyst which is used in the reaction system is provided in an amount sufficient to catalyze the reaction under the conditions set forth. Generally, this is an amount of from about 0.1 to 5 percent by weight of the alkali metal amide. The balance may be a support such as carbon.

Although not intending to be bound by theory, it is believed the first phase of the reaction is the formation of an alkali metal salt of an aromatic amine and the second phase is the liberation of the amine by protonation of the salt. Since hydrogen is a by-product of the reaction, and the reaction equilibrium is influenced by hydrogen concentration, it is preferably to maintain the hydrogen concentration as low as possible and remove it as it is formed. Removal of the hydrogen from the reaction medium can be effected through a physical or chemical means. For example, one physical technique is to reflux the reaction medium and effect condensation of the reaction product and exhaust the hydrogen from the reactor. A chemical acceptor for removing hydrogen can also be used and an example is copper oxide.

EXAMPLES

A series of amination runs were carried out in a 300 cc high pressure reactor manufactured by Autoclave Engineers. It was equipped with a Magnedrive strirrer fitted with a copper insert to prevent corrosion of the stainless steel body.

Initially, the reactor was purged with nitrogen and pressurized to a preselected nitrogen pressure in a range from 250 to 1200 psig. After pressurization, the mononuclear aromatic compound and catalyst was charged to the vessel. Care was taken to insure that the aromatic compound was completely anhydrous; this was effected through the use of a Dean Stark trap. Moderate agitation (500 RPM) was commenced. (This procedure was taken to avoid the formation of explosive peroxides generated when sodium amide is contacted with water.)

Another technique to adding the catalyst simultaneously with the aromatic compound was to add the catalyst separately. Both techniques were used interchangeably in carrying out the series of runs. However, in all cases the catalyst was dried prior to introduction to the reactor.

After the aromatic compound and catalyst were charged to the reactor, a portion of sodium amide was then added to the reactor. Again, care was taken so that the sodium amide would not be exposed to the atmosphere or moisture at any time during the charging of the autoclave. Once charged, the reactor was heated to the reaction temperature, the pressure being set by the vapor pressure of the aromatic compound.

The reaction was usually carried out overnight, e.g., 16 hours, and afterward the contents were cooled and the reactor vented. Some water was added to the reaction mixture by means of a small pump to destroy any remaining sodium salts which might be present in the system. Additional water was added, as necessary to dissolve the contents of the reactor and the reaction mixture filtered to remove particulates. The filtrate was treated with three 100 ml portions of methylene chloride and the aqueous layer then being acidified with dilute sulfuric acid. The treatment procedure was repeated using three 100 ml portions of methylene chloride and then dried, filtered and concentrated before analysis by gas chromotography.

The analysis of the reaction product was made with a Perkins-Elmer Sigma I gas chromtograph (GC) using a flame ionization detector and a Hewlett Packard silica capillary column with a Carbowax 20 stationary phase. The system was then calibrated against known compositions prior to analyzing the reaction mixture. A mass spectrometer (MSL) was also used for analyzing some runs.

Table I provides the results. The reaction conditions are specified in terms of reaction pressure, amounts of reactants in grams (g), reactants empolyed, catalysts, etc.

The $CoCO_3$ catalyst was prepared by reducing equal molar amounts of a cobalt precipitate of the salts of $CaCO_3$ and $CoCO_3$ in an atmosphere of hydrogen at 320° C.

The Rh/C catalyst was a commercial catalyst comprising 5% by weight rhodium on carbon powder and marketed by Oxy-Catalyst, Inc.

TABLE I

| RUNS | AROMATIC COMPOUND | AMIDE | CATALYST | COMMENTS |
|---|---|---|---|---|
| 1 | Toluene (50 g) + | $NaNH_2$ (20 g) | Rh/C (5 g dry) | Nickel plated liner, Trace only toluidines |
| 2 | Toluene (50 g) + | $NaNH_2$ (20 g) | Rh/C (5 g dry) | Numerous side products |
| *3 | Toluene (46 g) + | $NaNH_2$ (20 g) | $Co/CaCO_3$ (3 g) | Small amounts aniline, m-toluidine |
| 4 | Aniline (40–45 g) + | $NaNH_2$ (40 g) | Rh/C (5 g) | Exotherm, No recognizable products |
| 5 | Aniline (4.71 g) + | $NaNH_2$ (1.93 g) | Rh/C dry (2 g) | Gas off, Quench in water, extract. Aniline + unknown |
| 6 | Pyridine (2 g) + | $NaNH_2$ | None | Aminopyridine identified by gc/ms |
| 7 | Aniline (4.6 g) + | $NaNH_2$ (3.9 g) | Rh/C (dry) (1.1 g) | Only aniline detected in product |
| 8 | Toluene (46 g) + | $NaNH_2$ (20 g) | Rh/C (5 b wet) | Water on catalyst destroyed sodium amide. Possible trace toluidine |
| 9 | Toluene (46 g) + | $NaNH_2$ (20 g) | Rh/C (5 g dry) | All toluidines present, GC/MS |

| RUN | REACTION PRESSURE | TEMPERATURE | REACTION TIME | COMMENTS |
|---|---|---|---|---|
| 1 | 200 psig | ave. 227° C. | 17 hrs. | Rh/C (driven by azeotroping off water with toluene |
| 2 | 350 psig | ave. 271° C. | 15.5 hrs. | |
| 3 | 300 psig | ave. 260° C. | 16 hrs. | catalyst prepare |

TABLE I-continued

| | | | | |
|---|---|---|---|---|
| 4 | 125 psig | ave. 270° C. | 12 hrs. | removed H$_2$O from Rh/C catalyst by azeotroping with aniline |
| 5 | This reaction carried out by mixing reactants at atm pressure and at room (25° C.) temperature. 300 cc reactor not used. | | | no nickel coating on copper insert; used cyclohexane to azeotrope catalyst |
| 6 | atm | 100° C. | 3 hrs. | without catalyst |
| 7 | atm | room mixing in dry box max. temp. 185–190° C. | ½ hr. | catalyst dried Dean-Stark trap with toluene |
| 8 | 250 psig | 245° C. | overnight 16 hrs. | catalyst wet |
| 9 | 200 psig | 245° C. | 14.5 hrs. | catalyst dried (toluene azeotrope |

*Note that some dealkylation of the aromatic ring occurred in run 3 with the cobalt catalyst.

What is claimed:

1. In a process for forming a mononuclear aromatic amine by reacting a mononuclear aromatic compound with an aminating agent under conditions effective for forming said mononuclear aromatic amine, the improvement which comprises:

forming an intermediate reaction product of a toluene amine by effecting reaction between toluene and an alkali metal amide in the presence of a metallic hydrogenation catalyst group consisting of nickel, rhodium and cobalt, said catalyst being present in a proportion of from 0.1 to 5% based upon the weight of said toluene; and adding a protonating agent to the reaction product in sufficient amount to form said toluene amine.

2. The process of claim 1 wherein said alkali metal amide is represented by the formula: MNH$_2$ where M is an alkali metal selected from the group consisting of sodium, lithium or potassium.

* * * * *